US00PP11890P2

(12) United States Plant Patent
Fruehwirth

(10) Patent No.: US PP11,890 P2
(45) Date of Patent: May 22, 2001

(54) POINSETTIA PLANT NAMED 'ECKACTON'

(75) Inventor: Franz Fruehwirth, Encinitas, CA (US)

(73) Assignee: Paul Ecke Ranch, Encinitas, CA (US)

( * ) Notice: Subject to any disclaimer, the term of this patent is extended or adjusted under 35 U.S.C. 154(b) by 0 days.

(21) Appl. No.: 09/432,709

(22) Filed: Nov. 2, 1999

(51) Int. Cl.[7] ..... A01H 5/00

(52) U.S. Cl. ..... Plt./307

(58) Field of Search ..... Plt./307

(56) References Cited

PUBLICATIONS

UPOV–ROM GTITM Computer Database 2000/04, GTI Jouve Retrieval Software, citation for 'Eckacton', Jun. 1999.*

* cited by examiner

*Primary Examiner*—Bruce R. Campell
*Assistant Examiner*—Anne Marie Grünberg
(74) *Attorney, Agent, or Firm*—C. A. Whealy

(57) ABSTRACT

A new and distinct cultivar of Poinsettia plant named 'Eckacton', characterized by its bright red bracts; early flowering, response time about 8.5 weeks; freely flowering habit; medium green leaves; upright, spreading, compact and freely branching plant habit; rounded canopy; and excellent postproduction longevity.

2 Drawing Sheets

BACKGROUND OF THE INVENTION

The present invention relates to a new and distinct cultivar of Poinsettia plant, botanically known as *Euphorbia pulcherrima* Willd., and hereinafter referred to by the name 'Eckacton'.

The new Poinsettia is a naturally-occurring sport of the commercial *Euphorbia pulcherrima* Willd. cultivar Bright Red Freedom, disclosed in U.S. Plant Pat. No. 10,572. The new Poinsettia was selected by the Inventor in a greenhouse in Encinitas, Calif., in 1997. The objective of the Inventor's Poinsettia development program is to create new Poinsettia cultivars having interesting bract and leaf display, color and form; strong and freely branching stems; and good post-production longevity.

Asexual reproduction of the new Poinsettia by terminal cuttings taken at Encinitas, Calif., has shown that the unique features of this new Poinsettia are stable and reproduced true to type in successive generations of asexual reproduction.

BRIEF SUMMARY OF THE INVENTION

The following traits have been repeatedly observed and are determined to be the unique characteristics of 'Eckacton'. These characteristics in combination distinguish 'Eckacton' as a new and distinct cultivar:

1. Bright red bracts.
2. Early flowering, response time about 8.5 weeks.
3. Medium green leaves.
4. Upright, spreading and compact plant habit; rounded canopy.
5. Freely branching habit.
6. Excellent postproduction longevity.

In side-by-side comparisons conducted in Encinitas, Calif., plants of the new Poinsettia differed from plants of the parent cultivar, Bright Red Freedom, in the following characteristics:

1. Leaf color of plants of the new Poinsettia is lighter than leaf color of plants of 'Bright Red Freedom'.

2. Bract color of plants of the new Poinsettia is more orange than bract color of plants of 'Bright Red Freedom'.
3. Plants of the new Poinsettia flower a few days later than plants of 'Bright Red Freedom'.

Plants of the new Poinsettia can be compared to plants of the cultivar 490, disclosed in U.S. Plant Pat. No. 7,825. However, in side-by-side comparisons conducted in Encinitas, Calif., plants of the new Poinsettia differed from plants of '490' in the following characteristics:

1. Plants of the new Poinsettia are shorter than plants of '490'.
2. Plants of the new Poinsettia have smaller and fewer leaves than plants of '490'.
3. Leaf color of plants of the new Poinsettia is lighter than leaf color of plants of '490'.
4. Bract color of plants of the new Poinsettia is more orange than bract color of plants of '490'.
5. Bracts of plants of the new Poinsettia are held more upright than plants of '490'.
6. Plants of the new Poinsettia flower about a week later than plants of '490'.

BRIEF DESCRIPTION OF THE PHOTOGRAPHS

The accompanying colored photographs illustrate the overall appearance of the new Poinsettia, showing the colors as true as it is reasonably possible to obtain in colored reproductions of this type.

The photograph at the top of the first sheet comprises a side perspective view of a typical plant of 'Eckacton'.

The photograph at the bottom of the first sheet comprises a top perspective view of a typical plant of 'Eckacton'.

The photograph on the second sheet is a close-up view of typical bracts and leaves of '490' (left) and 'Eckacton' (right). Bract and foliage colors in the photographs may differ from actual colors due to light reflectance.

DETAILED BOTANICAL DESCRIPTION

The new Poinsettia has not been observed under all possible environmental conditions. The phenotype may vary somewhat with variations in environment such as temperature, daylength and light intensity, without, however, any variance in genotype. The following observations and measurements are averages that describe plants grown in Encinitas, Calif., under commercial practice in a glass-covered greenhouse with day temperatures ranging from 21 to 27° C., night temperatures ranging from 18 to 20° C., and light levels about 4,000 foot-candles. Plants were grown in 16 cm-pots, pinched one time, and flowered under naturally lenghthening nights during the fall/early winter.

In the following description, color references are made to The Royal Horticultural Society Colour Chart except where general terms of ordinary dictionary significance are used.

Botanical classification: *Euphorbia pulcherrima* Willd. 'Eckacton'.

Parentage: Naturally-occurring sport of *Euphorbia pulcherrima* Willd. cultivar Bright Red Freedom, disclosed in U.S. Plant Pat. No. 10,572.

Propagation:

*Type cutting.*—Terminal cuttings.

*Time to initiate roots.*—Summer: About 12 to 18 days at 27° C. Winter: About 15 to 18 days at 24° C.

*Time to develop roots.*—Summer: About 26 days at 27° C. Winter: About 26 days at 27° C.

*Rooting habit.*—Freely branching, becoming fibrous with development.

Plant description:

*Plant form:*—Inverted triangle; rounded canopy.

*Growth habit.*—Upright and spreading; compact. Freely branching. Branching is enhanced by removing the shoot apex.

*Plant vigor.*—Moderate.

*Plant height.*—About 22 cm.

*Crop time.*—From unrooted cuttings to a flowering plant in a 16-cm container, about 16 weeks are required.

*Stem description.*—Strong stems. Number of lateral branches: About six lateral branches are formed after removal of the terminal apex. Lateral branch length: About 12 cm. Internode length: About 7.5 mm. Stem color: 146B.

*Foliage description.*—Quantity of leaves per lateral branch: About 8. Length: About 8 cm. Width: About 6 cm. Shape: Ovate or lobed. Apex: Acuminate. Base: Acute. Margin: Entire. Texture: Smooth, dull; very sparse pubescence on lower surface. Color: Young foliage, upper surface: Darker than 146A, darker than 146A. Young foliage, lower surface: 146B. Mature foliage, upper surface: 146A. Mature foliage, lower surface: 146B. Venation, upper surface: 146B. Venation, lower surface: 146C. Petiole: Length: About 2.5 cm. Diameter; About 2 mm. Color: 59A.

Inflorescence description:

*Inflorescence type and habit.*—Inflorescences are compound corymbs of cyathia with colored flower bracts subtending the cyathia.

*Natural flowering season.*—Autumn/winter in Northern Hemisphere. Flower initiation and development can be induced under long night conditions. Response time is about 8.5 weeks.

*Quantity of Inflorescences.*—One per lateral branch, usually about six per plant.

*Inflorescence size including bracts.*—Diameter: About 27 cm. Height (depth): About 4 cm.

*Flower bracts.*—Quantity of flower bracts per inflorescence: Usually about 10 primary bracts and about 6 smaller secondary bracts per inflorescence. Length, largest bracts: About 11.5 cm. Width, largest bracts: About 8.5 cm. Shape: Ovate or elliptic to lobed. Apex: Acuminate. Base: Acute. Margin: Entire. Texture: Smooth. Aspect: Somewhat upright. Color: Developing, upper surface: Brighter than 46B. Developing, lower surface: 42A. Mature, upper surface: Brighter than 45A, becoming 46B with subsequent development. Mature, lower surface: 47A.

*Cyathia.*—Quantity: Usually about 10 per corymb. Diameter of cyathia cluster: About 2.5 by 3 cm. Length: About 1.1 cm. Width: About 6 mm. Color: Immature: 144B. Mature: 144A. Peduncle: Length: About 4 mm. Aspect: Strong, erect. Color: 144B. Stamens: Stamen number: Five to ten with numerous stamenodes per cyathium. Anther length: About 1 mm. Anther shape: Oval. Another color: 45B. Amount of pollen: Moderate to scarce. Pollen color: 7A to 7B. Pistils: No pistillate flowers observed. Nectary color: 14A.

Disease resistance: Plants of the new Poinsettia have not been observed to be resistant to pathogens common to Poinsettias.

Postproduction longevity: Excellent; generally plants maintain good substance and bract color for about eight weeks under interior conditions.

It is claimed:

1. A new and distinct cultivar of Poinsettia plant named 'Eckacton', as illustrated and described.

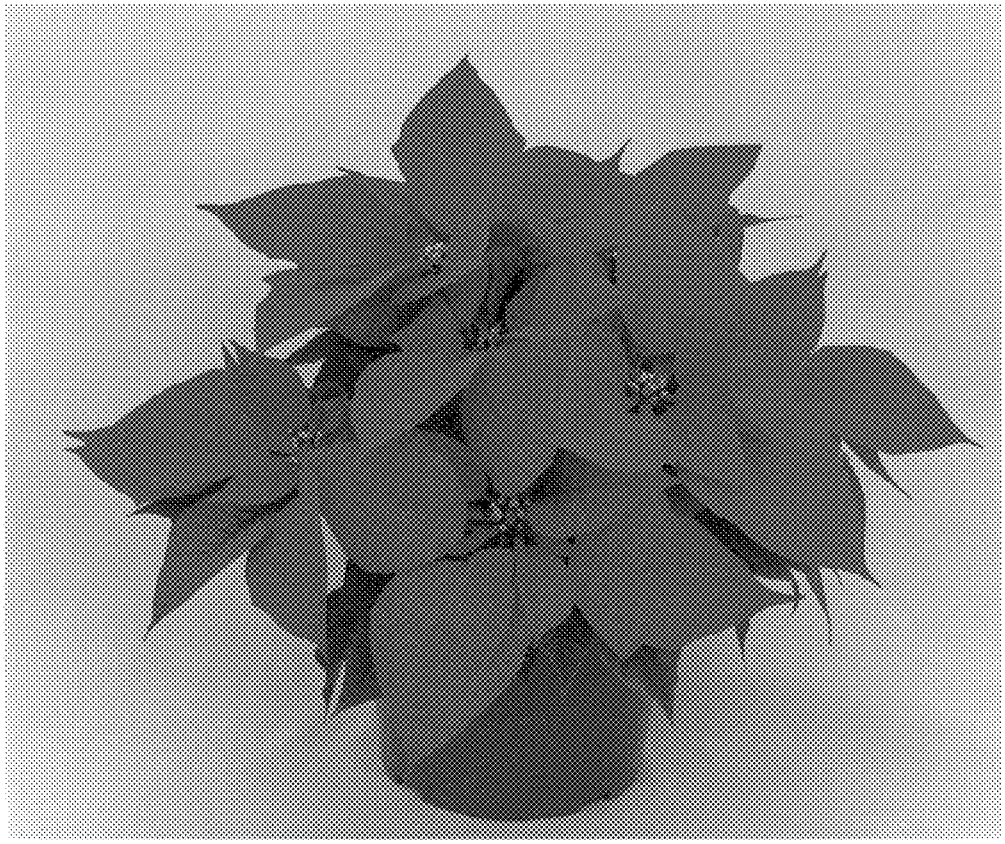
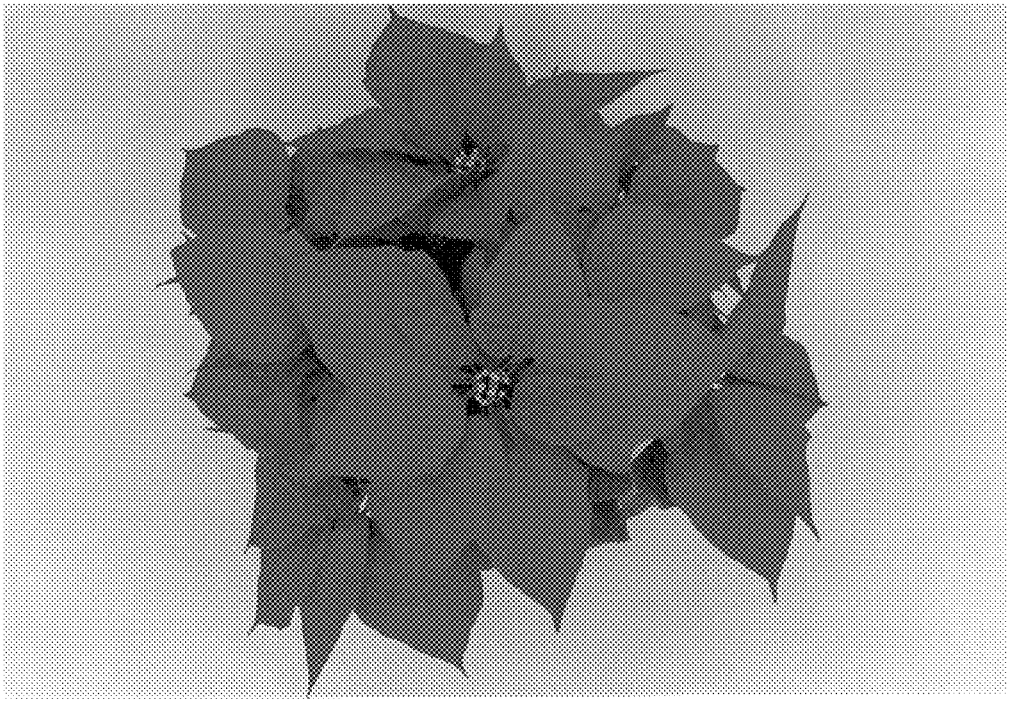

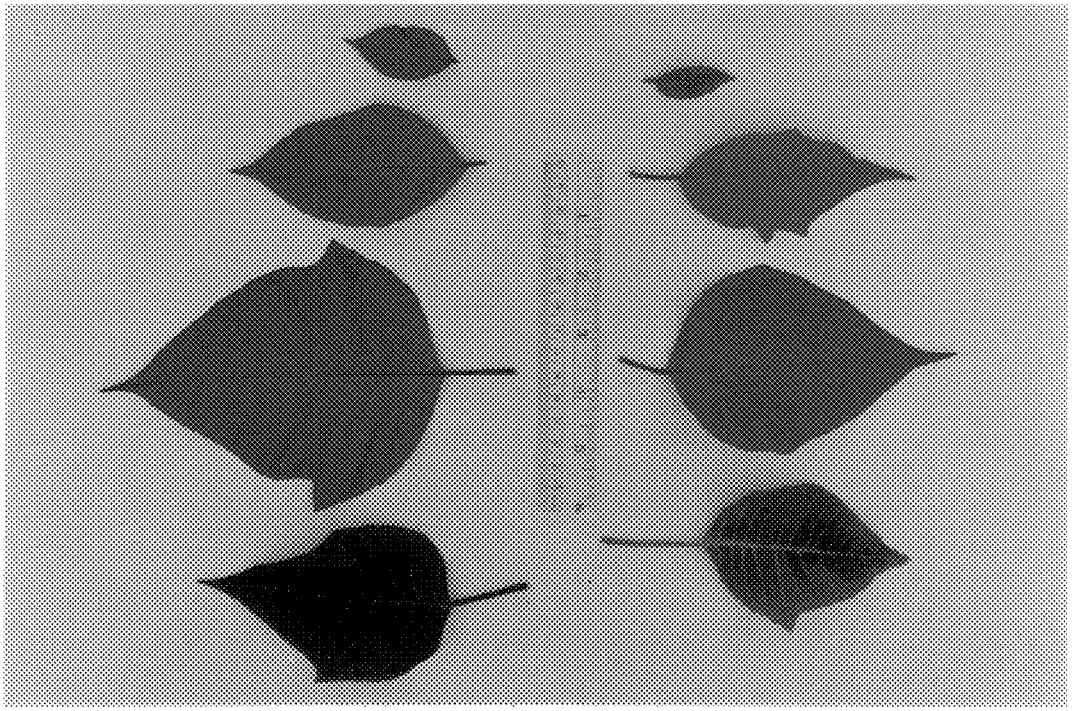

* * * * *